United States Patent [19]

Sielcken et al.

[11] Patent Number: 5,585,524
[45] Date of Patent: Dec. 17, 1996

[54] METHOD FOR THE PREPARATION OF AN ALDEHYDE

[75] Inventors: Otto E. Sielcken; Nicolaas F. Haasen, both of Sittard, Netherlands

[73] Assignee: DSM N.V., Netherlands

[21] Appl. No.: 494,186

Related U.S. Application Data

[63] Continuation of PCT/NL93/00258, Dec. 2, 1993.

[22] Filed: Jun. 23, 1995

[30] Foreign Application Priority Data

Dec. 23, 1992 [BE] Belgium .................................. 9201131

[51] Int. Cl.$^6$ ..................................................... C07C 45/49
[52] U.S. Cl. .......................................... 568/451; 560/175
[58] Field of Search ............................. 568/451; 560/175

[56] References Cited

U.S. PATENT DOCUMENTS

| | | | |
|---|---|---|---|
| 4,248,802 | 2/1981 | Kuntz | 568/454 |
| 5,057,618 | 10/1991 | Herrmann et al. | 556/21 |
| 5,177,228 | 1/1993 | Sato et al. | 568/454 |
| 5,235,113 | 8/1993 | Sato et al. | 568/454 |
| 5,354,908 | 10/1994 | Nadler | 568/451 |

OTHER PUBLICATIONS

Guo et al, J. Organometalic Chemistry, vol. 403, pp. 221–227 (1991).

*Primary Examiner*—James H. Reamer
*Attorney, Agent, or Firm*—Cushman Darby & Cushman IP Group of Pillsbury Madison & Sutro, LLP

[57] ABSTRACT

Method for the preparation of an aldehyde in a process in which cobalt is being recycled by:

(a) hydroformylating of an ethylenically unsaturated compound with carbon monoxide and hydrogen at a pressure higher than 5 MPa and a temperature higher than 80° C. in the presence of a cobalt carbonyl compound in an organic phase, following which (b) removing cobalt from the organic phase by contacting the organic phase with a polar mixture, which mixture is substantially immiscible with the organic phase, first the pressure being reduced to a pressure lower than 5 MPa and simultaneously or afterwards cooling being applied down to a temperature below 80° C., the polar mixture containing an organic ligand that is soluble in the polar mixture, and after which (c) separating the polar mixture from the organic phase, and after which (d) recovering the aldehyde from the organic phase and (e) contacting the cobalt-containing polar mixture with the organic phase, which phase is immiscible with the polar mixture, in the presence of carbon monoxide and at a pressure higher than 2 MPa, so that at least a part of the cobalt from the polar mixtures passes to the organic phase in the form of cobalt carbonyl, and (f) recycling the organic mixture to step (a).

25 Claims, No Drawings

METHOD FOR THE PREPARATION OF AN ALDEHYDE

RELATED APPLICATION

This application is a continuation of PCT/NL93/00258 filed Dec. 2, 1993.

FIELD OF THE INVENTION

The invention relates to a method for the preparation of an aldehyde in a process in which cobalt is being recycled by:

(a) hydroformylating an ethylenically unsaturated compound in a reaction zone with carbon monoxide and hydrogen at a pressure higher than 5 MPa and a temperature higher than 80° C. in the presence of a cobalt carbonyl compound in an organic phase, (b) removing cobalt from the organic phase by contacting the organic phase with a polar mixture, which mixture is substantially immiscible with the organic phase, under such conditions that practically all of the cobalt is incorporated in the polar mixture, (c) separating the polar mixture from the organic phase, (d) recovering the aldehyde from the organic phase, (e) contacting the cobalt-containing polar mixture with the organic phase, which phase is immiscible with the polar mixture, under such conditions that at least a part of the cobalt from the polar mixtures passes to the organic phase in the form of cobalt carbonyl, and (f) recycling the organic mixture to step (a).

BACKGROUND OF THE INVENTION

Such a process is described in Advanced Chemical Separations [Homogeneous Catalysis-II, Symp. 1973](1974), 132, 19–26). This article describes a method by which the cobalt is recovered from an organic phase after hydroformylation by mixing the organic phase with a (polar) mixture of diluted acetic acid and water in the presence of air. The cobalt carbonyl is oxidized to $Co^{+2}$, ending up in the water mixture as the corresponding salt (similar to step (b) of the invention). After a phase separation between the polar water mixture and the organic phase, the water mixture (similar to step (c)) is subsequently treated with carbon monoxide and hydrogen at a temperature of (150°–200° C.) and a pressure of 30 MPa, upon which cobalt is reduced to cobalt carbonyl (the so-called precarbonylation). This reaction is represented by formula (1):

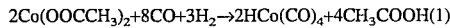

$$2Co(OOCCH_3)_2 + 8CO + 3H_2 \rightarrow 2HCo(CO)_4 + 4CH_3COOH \quad (1)$$

After this step the water mixture is contacted with an organic mixture, which mixture forms the feed for the hydroformylation reactor, upon which the cobalt carbonyl passes to the organic phase (similar to step (e)). The water mixture still containing unconverted $Co^{2+}$ and the organic mixture are separated by means of phase separation. The organic mixture is subsequently directed to the hydroformylation reactor (similar to step (f)).

A drawback of this known method is that a precarbonylation is needed. The precarbonylation reaction is slow and requires a high pressure, so that use must be made of big reactors that are suitable for high pressures.

SUMMARY AND OBJECTS OF THE INVENTION

The object of the invention is a method for the hydroformylation of an ethylenically unsaturated compound in which the cobalt catalyst can simply be recycled and in which precarbonylation is avoided.

Recovery of the cobalt catalyst from the reaction mixture after hydroformylation as described above is of great importance. The cobalt catalyst can be reused in the hydroformylation reaction and purification of the aldehyde is simplified if no cobalt catalyst is present.

According to the invention this object is achieved in that in step (b) first the pressure is reduced to below 5 MPa and simultaneously or afterwards cooling the temperature to below 80° C., wherein the polar mixture contains an organic ligand that is soluble in the polar mixture and wherein the ligand forms a complex with cobalt and wherein step (e) is conducted in the presence of carbon monoxide under a pressure higher than 2 MPa.

It has been found that precarbonylation is not needed when use is made of the method according to the invention. This has the advantage that the number of complicated process steps is reduced, so that the cobalt recycle can be carried out more simply. An added advantage is that there is no net water production and that no acetic acid is needed, as is the case in the method according to the above-mentioned article.

It is found that, if in step (b) first the pressure is reduced and then the temperature is reduced, a complex of cobalt and organic ligand is formed in the polar mixture, with the cobalt carbonyl decomposing in the organic phase. In step (e) this complex of cobalt and the organic ligand will decompose under the influence of elevated carbon monoxide and/or hydrogen pressure, yielding cobalt carbonyl which passes to the organic phase. Step (e) is also called re-extraction (e) and step (b) first extraction (b).

DETAILED DESCRIPTION OF THE INVENTION

The term organic phase stands for the substantially apolar portion of the mixture that is present in the reaction zone, leaves the reaction zone and is recycled in step (f). The organic phase may consist of non-converted ethylenically unsaturated compound, aldehyde, a solvent which may be apolar, cobalt carbonyl and hydrogenation products and heavy by-products formed in the process.

The use of an organic ligand, which ligand is soluble in a polar mixture, during hydroformylation of an olefin in the presence of a cobalt carbonyl catalyst is described in Journal of Organometallic Chemistry, 403 (1991) 221–227. This article advises against use of a method resembling the method according to the invention because much cobalt would remain behind in the organic phase after separation of the polar mixture in step (c). Loss of cobalt results in a lower activity of the cobalt being recycled. However, it has been found that if the first extraction (b) is carried out in accordance with the method according to the invention, the amount of cobalt in the organic phase after the first extraction is virtually zero.

Experiment 41 of EP-A-372.313 describes a method which uses cobalt carbonyl and an organic ligand dissolved in a polar water mixture during hydroformylation of 1-hexene. After the reaction the first extraction (similar to step (b) of the present invention) is carried out according to a method disclosed in DE-A-2627354. In this method, first—in contrast with the method according to the invention—the mixture is cooled from 110° C. down to 20° C. and subsequently the pressure is reduced. Next, the aqueous phase is separated (similar to step (c)). The aqueous phase, in which the organic ligand and the cobalt are dissolved, is then reused for hydroformylation of 1-hexene (similar to steps (d, e, a)). It now appears that in this second reaction the ratio between normal aldehyde and branched aldehydes (n/b ratio) decreases from 3.4:1 to 2.1:1.

For a similar process as that disclosed in EP-A-372.313 such a reduction of the n/b ratio is found in a process as described in La Chimica E L'Industria V. 60, N 11. November 1978, column 2, page 889, in which the first extraction (similar to step (b)) is carried out at 100° C. and the re-extraction in the presence of carbon dioxide.

When the method according to the invention is used, however, the n/b ratio proves to remain virtually constant after the cobalt has been reused several times.

Compared with the above-mentioned methods the method according to the invention has the advantage that the cobalt can be recycled in a simple manner. Recycling is simple because, apart from the carbon monoxide and hydrogen needed for hydroformylation, no additional substances are to be added to the polar mixture during recycling in order to enable the first extraction (b) and/or the re-extraction (e). Another important advantage of the method is that the activity (aldehyde production) and selectivity (n/b ratio) of the hydroformylation reaction does not decrease when cobalt is being recycled. A constant production of aldehydes and a constant n/b ratio when cobalt is being recycled are important conditions to be met if a hydroformylation process is to be suitable for industrial application. Normal aldehyde as a rule being the target product, a decreasing n/b ratio will be undesirable.

The polar mixture can be any polar liquid that is substantially immiscible with the apolar organic phase under the process conditions of the first extraction (b). Preferably, the polar mixture is water.

The ethylenically unsaturated compound can be a dialkene, alkene or a cycloalkene with 3 to 30 carbon atoms and preferably 3 to 12 carbon atoms. Examples of suitable alkenes and dialkenes are propene, butene, butadiene, pentene, hexene, octene and dodecene. Examples of suitable cycloalkenes are cyclopentene, cyclohexene, cyclooctene and cyclododecene. Examples of other ethylenically unsaturated compounds are dialkenes in which the two unsaturated compounds are non-conjugated, styrene, alpha-methyl styrene, acrylic acid, methacrylic acid and preferably the alkyl esters of these acids.

Preferably, the ethylenically unsaturated compound is an alkene carboxylic acid ester of the following chemical formula

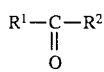  (2)

where $R^1$ is a mono- or polyunsaturated, branched or unbranched acyclic hydrocarbon group with 2 to 11 carbon atoms, and $R^2$ represents an alkyl group with 1 to 8 carbon atoms or an aryl group with 6 to 10 carbon atoms. Preferably $R^1$ has 5 carbon atoms and $R^2$ is an alkyl group with 1 to 8 carbon atoms or a phenyl group. Examples of suitable alkene carboxylic acid esters are the 2-, 3- and 4-pentenoic acid esters and branched pentenoic acid esters, in which $R^2$ can represent a methyl, ethyl, propyl, isopropyl, n-butyl, tert. butyl, isobutyl, cyclohexyl and phenyl group.

The pentenoic acid esters are important because the 5-formyl valeric acid ester is formed by the method according to the invention. The 5-formylvaleric acid ester is important because this compound may serve as starting material for the preparation of caprolactam, caprolactone or adipic acid.

The molar ratio between cobalt and the ethylenically unsaturated compound in the organic phase is generally between 1:5 and 1:10,000. Preferably, this ratio is between 1:10 and 1:1000.

The organic ligand is soluble in the polar mixture and can form a coordinated complex with cobalt. The organic ligand is preferably not soluble or hardly soluble in the non-polar organic phase under the conditions of the first extraction (b) since otherwise the ligand losses in step (c) would become too great. The organic ligand generally has substituted ionizable groups on account of which the ligand is soluble in the polar mixture. Suitable ligands that are soluble in polar mixtures have the general structural formulas (3) and (4):

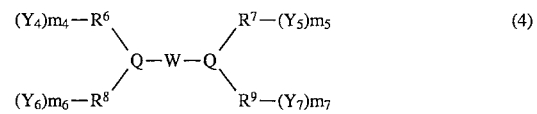

where $R^3$, $R^4$ and $R^5$ of formula (3) and $R^6$, $R^7$, $R^8$ and $R^9$ of formula (4) independently represent a hydrocarbon group with 1 to 30 carbon atoms and where the hydrocarbon group can represent an alkyl, aryl, alkaryl, aralkyl and cycloalkyl, where W in formula (4) represents a bivalent organic bridging group, where Q represents an atom chosen from the group formed by P, As and Sb and where Y1, Y2 and Y3 of formula (3) and Y4, Y5, Y6 and Y7 of formula (4) represent ionic groups that are substituted on the hydrocarbon group, which ionic groups can be chosen from the group formed by: —$SO_3M$, —$PO_3M$, $CO_2M$ and —$N(R^{10})_3X$, where M represents an inorganic or organic cation and X represents an inorganic or organic anion, M and X being chosen such that the ligand becomes soluble in the polar mixture and $R^{10}$ represents a hydrocarbon group with 1 to 30 carbon atoms, where the hydrocarbon group can represent an alkyl, aryl, alkaryl, aralkyl and cycloalkyl, where m1, m2, m3, m4, m5, m6 and m7 represent integers which independently are between 0 and 5, where at least one of m1, m2 and m3 in (3) not being zero or at least one of m4, m5, m6 and m7 in (4) not being zero. The integers m1 to m7 represent the number of ligand groups capable of ionization and their value must be high enough for the ligand to be soluble in the polar mixture.

The hydrocarbon groups $R^3$ to $R^9$ as a rule have 1 to 18 carbon atoms and preferably 1 to 12 carbon atoms. Examples of suitable groups are methyl, ethyl, propyl, butyl, hexyl, cyclohexyl and phenyl. Preferably, at least one of the group formed by $R^3$, $R^4$, and $R^5$ and at least one of the group formed by $R^6$, $R^7$, $R^8$ and $R^9$ is a phenyl group. More preferably, at least two, and in particular all groups of the series $R^3$, $R^4$, and $R^5$ are phenyl groups, and at least three and in particular all groups of the series $R^6$, $R^7$, $R^8$ and $R^9$ are phenyl groups.

The bivalent bridging group (W) is a bivalent group consisting of 1 to 30 carbon atoms. Examples of suitable bivalent groups are a hydrocarbon group or a hydrocarbon group containing oxygen, sulphur or nitrogen, with two hydrocarbon groups being coupled by, respectively, the oxygen atom, the sulphur atom or the nitrogen atom. Preferably, the hydrocarbon group has 1 to 16 and more preferably 1 to 12 carbon atoms. A particularly suitable group which can serve as bridging group W is the bivalent alkyl group with 2 to 8 carbon atoms. Preferably, Q is a phosphorus atom.

The organic ligand is generally a salt, the cation (M) being chosen from the group of alkali metal and alkaline earth metals such as Li, Na, K, Cs, Rb, Ca, Ba, Mg and St, and the ammonium cation and anion (X) being chosen from the group formed by sulphate, carbonate, chloride, acetate and oxalate.

Examples of suitable organic ligands are the salts of sulphonated and carboxylated triaryl phosphines. Suitable sulphonated triaryl phosphines are triphenyl phosphines with 1 to 6 sulphonate groups. Examples of such phosphines are monosulphonphenyl diphenyl phosphine, di(monosulphonphenyl)phenyl phosphine, tri(monosulphonphenyl)phosphine and di(trisulphonphenyl)phenyl phosphine.

Suitable carboxylated triaryl phosphines are triphenyl phosphines with 1 to 6 carboxylate groups. Examples of such phosphines are monocarboxylphenyl diphenyl phosphine, di(monocarboxylphenyl) phenyl phosphine, tri-(monocarboxylphenyl)phosphine and di(tricarboxylphenyl)phenyl phosphine.

The molar ratio of organic ligand to cobalt is generally between 1:1 and 10:1. Preferably, this ratio is between 1:1 and 3:1.

The various steps of the method according to the invention can be carried out both batchwise and continuously. Preferably, the process is carried out continuously.

The invention will be elucidated stepwise (a→e). For the conditions of the hydroformylation reaction in step (a) use can be made of the generally known hydroformylation conditions as described, inter alia, in EP-A-295.551 and EP-A-295.549. Step (a) is generally carried out at a temperature between 60° and 200° C. and preferably between 80° and 150° C. The pressure is generally between 5.0 and 50 MPa and preferably between 5.0 and 30 MPa.

If desired the hydroformylation reaction can be carried out in the presence of an organic solvent which is virtually immiscible with the polar mixture. Suitable organic solvents are ketones, acetophenone and cyclohexanone; ethers such as diethyl ether, anisole and diphenyl ether; aromatic compounds such as benzene, toluene and xylene; paraffins such as hexane, heptane, cyclohexane, methyl cyclohexane and iso-octane and esters such as methyl benzoate and methyl valerate. Preferably, use is made of aromatic and/or paraffinic solvents. Use can be made of mixtures of solvents.

The hydroformylation is carried out in the absence or presence of additional ligands besides carbon monoxide and besides the organic ligand soluble in the polar mixture in the organic phase. It has been found that if the hydroformylation is carried out in accordance with the method according to the invention, it is preferred to do without an additional ligand, in the organic phase.

The molar ratio of the ethylenically unsaturated compound to carbon monoxide during the hydroformylation reaction will generally be between 1:10 and 10:1, and preferably between 2:1 and 1:5.

The molar ratio of carbon monoxide to hydrogen during the hydroformylation reaction is generally between 1:0.5 and 1:10. Preferably, this ratio is between 1:1 and 1:2.

In case of a batchwise process the reaction zone where hydroformylation takes place can take the form of a stirred vessel. In case of a continuous process a stirred tank reactor (CSTR), a tubular reactor, a non-stirred bubble column and an internal or external gas-lift loop reactor.

The organic phase leaving the reaction zone contains at least aldehyde and non-converted ethylenically unsaturated compound and cobalt carbonyl. This mixture is contacted in first extraction (b) with the polar mixture from re-extraction (e). This is understood to include a method in which the polar mixture after re-extraction (e) is not separated from the organic phase and also forms part of the feed to the reaction zone (step (a)). Since the pressure, and thus the partial pressure of hydrogen and carbon monoxide, is first reduced in the first extraction (b), while the temperature is reduced simultaneously or only afterwards, virtually all of the cobalt appears to end up in the polar mixture. It is important that while the pressure is being reduced in the first extraction (b) there is already sufficient contact between the polar mixture and the organic phase so as to give the cobalt the opportunity to pass to the polar mixture. It is preferred to effect the separation of the polar mixture and the organic phase, for instance by phase separation, in step (c) carefully so that the amount of polar mixture, which contains cobalt, that remains behind in the organic phase is minimal. The reason for this is that during working up of aldehyde in step (d) cobalt is found to catalyze some side reactions, giving rise to the formation of byproducts. Another reason is that any cobalt remaining behind in the organic phase can be recovered only with difficulty, so that fresh cobalt needs to be added to the cycle to keep the activity of the hydroformylation reaction at a constant level.

The weight ratio of the polar solution used in first extraction (b) to the organic phase in which the hydroformylation reaction takes place is between 1:10 and 10:1, and preferably between 1:5 and 5:1.

During the first extraction (b) the pressure is reduced to a pressure lower than the pressure used during the hydroformylation reaction. This pressure is generally between 0.01 and 5.0 MPa and preferably between 0.05 and 0.5 MPa. The pressure is reduced by separating gaseous components, such as carbon monoxide and hydrogen. On account of this pressure reduction some degree of cooling will generally take place. Further cooling can be achieved, for instance, by means of cooling elements. Carbon monoxide that is released during the extraction step is preferably separated simultaneously. It is important that the pressure is not reduced too far at a relatively high temperature because otherwise there is a risk that volatile cobalt compounds are evaporated and lost. To prevent evaporation of the volatile cobalt compounds, after a certain pressure reduction the temperature can be reduced, followed by further pressure reduction.

In the first extraction (b) the temperature is reduced to below 80° C. The lower limit is not critical, but usually the temperature will not be reduced further than to 0° C. In general the temperature is reduced to a temperature that is between 20° and 80° C.

The first extraction (b) can, for instance, be carried out continuously in a series of mixers followed by a settler. In the subsequent mixers the pressure would be reduced stepwise with simultaneous cooling. A batchwise extraction could be carried out, for instance, in a stirred vessel.

After the first extraction (b) aldehyde is separated, in step (d), from the organic phase that has been freed from cobalt. The cobalt having been removed from the organic phase, it is possible to recover the aldehyde by means of a distillation without any byproducts being formed. After the aldehyde and any byproducts have been isolated, the residual organic phase, which phase generally contains as yet non-converted ethylenically unsaturated compound and a solvent, if any, is recycled to step (e) or direct to step (a). It goes without saying that, depending on the solvent, in some cases the solvent is not separated from the aldehyde simultaneously with the non-converted ethylenically unsaturated compound.

In the re-extraction (e) an organic phase is contacted with the cobalt-containing polar mixture from the first extraction (b) in the presence of carbon monoxide and hydrogen at a pressure higher than 5 MPa. This will result, under the influence of the elevated pressure, in formation of cobalt carbonyl, which cobalt carbonyl will pass to the organic mixture. After re-extraction (e) the polar mixture and the organic phase are separated, the organic phase being led to the reaction zone while the polar mixture is recycled to the first extraction (b).

The organic phase used in the first extraction (e) may contain fresh, ethylenically unsaturated compound, a solvent, if any, or the ethylenically unsaturated compound of step (f) that has not been converted during hydroformylation, or combinations of these components. After re-extraction (e) if desired one or more of these components can be added to the organic phase before the organic phase is led to the reaction zone (step (a)).

The temperature at which re-extraction (e) is carried out is generally between 50° and 200° C. Preferably, the temperature is the same as the temperature at which the hydroformylation reaction is carried out. It is important that the carbon monoxide pressure at which re-extraction (e) is carried out is sufficiently high, so that at least a portion of the complex of organic ligand and cobalt in the polar mixture is decomposed and the cobalt carbonyl is formed. The pressure in re-extraction (e) will therefore be higher than 2 MPa, and preferably be higher than 5 MPa. The upper limit is not critical but will generally not be substantially higher than the pressure used during hydroformylation (a). In general, under normal operating conditions not all the cobalt contained in the polar mixture will pass to the organic phase. However, this is not objectionable, for the polar mixture is recycled to step (b) so that the cobalt is not lost.

In a first embodiment of step (e) no hydrogen is present during re-extraction (e) so as to avoid premature hydroformylation.

In a second embodiment of step (e) the re-extraction (e) is carried out in two steps, first the polar mixture being treated with carbon monoxide and hydrogen at a pressure of 2 to 20 MPa and a temperature of 80° to 150° C., yielding cobalt carbonyl, and this mixture subsequently being contacted with the organic phase in the absence of carbon monoxide and hydrogen. This obviates the need for a separate carbon monoxide flow, besides a carbon monoxide/hydrogen flow, in the process.

The re-extraction (e) according to, for instance, one of the above embodiments can, for instance, be a continuous operation in a counterflow extraction column or in a mixer-settler. Batchwise extraction could, for instance, be carried out in a stirred vessel.

In a third embodiment of step (e), which is preferred the re-extraction (e) and step (a) are combined in one process step. In that case the reaction zone is therefore fed with the cobalt-containing polar mixture from first extraction (b) and the organic phase, which organic phase contains at least the ethylenically unsaturated compound. This has the advantage that the number of process steps is reduced. The conditions in such a combined process step are the same as the conditions, already described, for step (a).

The embodiment, in which steps (e) and (a) are combined, of the invention that is preferred will be explained on the basis of FIG. 1.

Via flow 1 fresh, ethylenically unsaturated compound is led to reaction zone A. In reaction zone A simultaneously step (a) and re-extraction (e) are carried out. In apparatus B the pressure is reduced and simultaneously or afterwards the temperature is reduced and the polar mixture and the organic phase are separated. The cobalt-free organic phase is passed to separation section C via flow 3. Via flow 5 the cobalt-containing polar mixture is recycled to reaction zone A. In separation zone C the aldehyde is recovered and discharged by means of flow 4. Any byproducts can also be recovered in separation section C (not shown in FIG. 1). Via flow 6 the aldehyde-free organic phase is recycled to reaction zone A.

EXAMPLES

The invention will be elucidated in the following examples. These examples shall not be considered to limit the invention.

In the examples the sodium salt of tri(monosulphonphenyl) phosphine $(P(m-C_6H_6SO_3Na)_3=TPPTS)$ is used as organic ligand. The sodium salt of tri(monosulphonphenyl)phosphine was prepared as described in U.S. Pat. No. 4,248,802. In the examples use is further made of the following terms as defined below:

$$PE/Co = \frac{\text{mmol 3-pentenoic acid methyl ester}}{\text{mmol cobalt}} \quad (5)$$

$$L/CO = \frac{\text{mmol TPPTS}}{\text{mmol cobalt}}$$

Example I

Into a glass liner 0.15 mmol of the catalyst precursor $CO_2(CO)_8$, 0.69 mmol TPPTS (ligand, L) and 4.7 g of toluene were introduced, so that the L/Co ratio in the resulting mixture was 2.3. After all the $CO_2(CO)_8$ had dissolved, 6.1 g of demineralized distilled water was added. The liner was placed in a 50-ml mechanically stirred Parr autoclave (fully made of Hastelloy-C steel). The autoclave was purged three times with a 1:1 $CO/H_2$ mixture. Subsequently, at a $CO/H_2$ (1:1) pressure of 5.5 MPa and a stirring speed of 1250 rpm, the temperature of the autoclave was raised to 110° C. After 30 minutes a mixture of 2.4 g of toluene, 2.8 g of 3-pentenoic acid methyl ester (PE) and 0.3 g of an internal standard nonane was injected into the autoclave, the reaction pressure in the autoclave being raised to 6.5 MPa. The amount of 3-pentenoic acid methyl ester had been chosen so that the PE/CO ratio in the resulting mixture was 81. After 5 hours the reaction was stopped by reducing the pressure to 5 MPa and then cooling the autoclave down to 80° C. Subsequently, the pressure was reduced further to 0.5 MPa, followed by cooling down to 25° C. After 1 minute the vessel was opened; it was found that complete phase separation had taken place, yielding a colourless organic phase and a brown/red aqueous phase (polar phase). Phase separation had resulted in less than 0.1% of the initial amount of cobalt remaining behind in the organic phase. The mixtures were analyzed by means of gas chromatography and gas chromatograph-mass spectrometry. The results are presented in Table I.

Example II

Example I was repeated with an L/Co ratio of 1.6 and a PE/Co ratio of 56 at a reaction pressure of 6.5 MPa and a temperature of 120° C. for 6 hours. The total reaction mixture contained 2.6 g of 3-pentenoic acid methyl ester, 0.4 g of nonane, 7.9 g of toluene, 6.3 g of water, 0.21 mmol $Co_2(CO)_8$ and 0.66 mmol TPPTS. The results are presented in Table I.

Example III

Example I was repeated with an L/Co ratio of 1.7 and a PE/Co ratio of 53 at a reaction pressure of 6.5 MPa and a temperature of 120° C. for 6 hours. The total reaction mixture contained 1.8 g of 3-pentenoic acid methyl ester, 0.4 g of nonane, 12.4 g of toluene, 5.7 g of water, 0.15 mmol $Co_2(CO)_8$ and 0.51 mmol TPPTS. The results are presented in Table I.

Example IV

Example I was repeated with an L/Co ratio of 1.1 and a PE/Co ratio of 20 at a reaction pressure of 6.5 MPa and a temperature of 120° C. for 6 hours and 30 minutes. The total reaction mixture contained 1.73 g of 3-pentenoic acid methyl ester, 0.35 g of nonane, 11.3 g of toluene, 7.0 g of water, 0.38 mmol $Co_2(CO)_8$ and 0.85 mmol TPPTS. The results are presented in Table I.

Example V

Example I was repeated with an L/Co ratio of 1.5 and a PE/Co ratio of 45 at a reaction pressure of 12.0 MPa and a temperature of 120° C. for 5 hours. The total reaction mixture contained 1.73 g of 3-pentenoic acid methyl ester, 0.3 g of nonane, 11.4 g of toluene, 6.7 g of water, 0.17 mmol $Co_2(CO)_8$ and 0.5 mmol TPPTS. The results are presented in Table I.

Example VI

Example I was repeated with an L/Co ratio of 1.2 and a PE/Co ratio of 12 at a reaction pressure of 12.0 MPa and a temperature of 120° C. for 5 hours. The total reaction mixture contained 0.52 g of 3-pentenoic acid methyl ester, 0.4 g of nonane, 12.6 g of toluene, 7.5 g of water, 0.19 mmol $Co_2(CO)_8$ and 0.47 mmol TPPTS. The results are presented in Table I.

Example VII

Example I was repeated with an L/Co ratio of 1.7 and a PE/Co ratio of 44 at a reaction pressure of 6.5 MPa and a temperature of 120° C. for 5 hours. The total reaction mixture contained 1.75 g of 3-pentenoic acid methyl ester, 0.3 g of nonane, 11.4 g of toluene, 6.9 g of water, 0.18 mmol $Co_2(CO)_8$ and 0.32 mmol TPPTS. The results are presented in Table I.

Example VIII

Example VII was repeated, the liner this time being filled with the water mixture separated in Example VII. Toluene was dosed separately so that the amount of toluene present was the same as in Example VII. The PE/Co ratio was 45. The total reaction mixture contained the aqueous phase of Example VII and 1.75 g of 3-pentenoic acid methyl ester, 11.4 g of toluene and 0.34 g of nonane. The results are presented in Table I.

Example IX

Example VII was repeated, the liner this time being filled with the water mixture separated in Example VIII. Toluene was dosed separately so that the amount of toluene present was the same as in Example VII. The PE/Co ratio was 44. The reaction mixture contained the aqueous phase of Example VIII and 1.71 g of 3-pentenoic acid methyl ester, 0.3 g of nonane and 11.2 g of toluene. The results are presented in Table I.

Example X

Example I was repeated with an L/Co ratio of 1.2 and a PE/Co ratio of 79 at a reaction pressure of 12.0 MPa and a temperature of 120° C. for 7 hours. The reaction mixture contained 3.0 g of 3-pentenoic acid methyl ester, 0.54 g of nonane, 6.6 g of toluene, 6.9 g of water, 0.16 mmol $Co_2(CO)_8$ and 0.60 mmol TPPTS. The results are presented in Table I.

Example XI

Example X was repeated, the liner this time being filled with the water mixture separated in Example X. Toluene was dosed separately so that the amount of toluene present was the same as in Example X. The reaction time was 7 hours. The reaction mixture contained the aqueous phase of Example X and 3.0 g of 3-pentenoic acid methyl ester, 0.54 g of nonane and 2.7 g of toluene. The results are presented in Table I.

Comparative Experiment A

Example I was repeated, no organic ligand being added, with a PE/Co ratio of 59 at a reaction pressure of 6.5 MPa and a temperature of 110° C. for 5 hours. The reaction mixture contained 1.75 g of 3-pentenoic acid methyl ester, 0.4 g of nonane, 7.0 g of toluene, 6.9 g of water and 0.18 mmol $Co_2(Co)_8$. After phase separation 95 to 100% of the original amount of cobalt was found to be present in the organic phase. The other results are presented in Table I.

Comparative Experiment B

Experiment A was repeated, no demineralized distilled water and no organic ligand being added, with a PE/Co ratio of 59 at a reaction pressure of 6.5 MPa and a temperature of 110° C. for 2 hours. The reaction mixture contained 2.0 g of 3-pentenoic acid methyl ester, 0.35 g of nonane, 14.0 g of toluene and 0.15 mmol TPPTS. After the reaction no two separate phases were present. The results are given in Table I. This means 100% of the cobalt was present in the organic phase.

TABLE 1

| Example | conv.[1] | tot-A | n-A | MV | Co |
|---|---|---|---|---|---|
| I | 25 | 96 | 68 | 3 | <0.1 |
| II | 56 | 96 | 67 | 3 | <0.2 |
| III | 36 | 96 | 70 | 3 | <0.1 |
| IV | 82 | 93 | 67 | 3 | <0.2 |
| V | 52 | 96 | 71 | 3 | <0.2 |
| VI | 45 | 96 | 72 | 4 | <0.2 |
| VII | 31 | 96 | 71 | 3 | <0.1 |
| VIII | 33 | 96 | 70 | 3 | <0.1 |
| IX | 34 | 96 | 71 | 3 | <0.1 |
| X | 73 | 85 | 60 | 3 | <0.3 |
| XI | 76 | 86 | 61 | 2 | <0.1 |
| A | 74 | 92 | 68 | 3 | 95–100 |
| B | 39 | 96 | 71 | 3 | 100 |

[1] conv. + mol % conversion of 3-pentenoic acid methyl ester,
tot-A = mol % aldehydes relative to total of products,
n-A = % normal aldehydes of total of aldehydes,
MV = mol % methyl valerate relative to total of products,
Co = fraction (expressed in percents) of cobalt in organic phase after phase separation.

The examples show that in the process according to the invention cobalt can be reused without any decrease in the selectivity and activity of the catalyst. The examples show that the presence of the organic ligand-containing water mixture has almost no effect on the selectivity and activity of the hydroformylation reaction, since corresponding results were obtained in comparative experiment B (where these components are absent).

Example XII

Example I was repeated, without toluene being added as solvent, with an L/Co ratio of 1.1 and a PE/Co ratio of 124 at a reaction pressure of 6.5 MPa and a temperature of 120°

C. for 5 hours. The reaction mixture contained 9.06 g of 3-pentenoic acid methyl ester, 0.8 g of nonane, 6.5 g of water, 0.28 mmol $Co_2(CO)_8$ and 0.63 mmol TPPTS. The results are presented in Table 2.

Example XIII

Example I was repeated, without toluene being added as solvent, with an L/Co ratio of 1.2 and a PE/Co ratio of 149 at a reaction pressure of 12.0 MPa and a temperature of 120° C. for 5 hours. The reaction mixture contained 9.7 g of 3-pentenoic acid methyl ester, 0.97 g of nonane, 6.9 g of water, 0.29 mmol of $Co_2(CO)_8$ and 0.71 mmol TPPTS. The results are presented in Table 2.

Example XIV

Example I was repeated, without toluene being added as solvent, with an L/Co ratio of 1.1 and a PE/Co ratio of 126 at a reaction pressure of 13.0 MPa and a temperature of 120° C. for 3 hours. The reaction mixture contained 9.47 g of 3-pentenoic acid methyl ester, 0.95 g of nonane, 6.16 g of water, 0.30 mmol $Co_2(CO)_8$ and 0.63 mmol TPPTS. The results are presented in Table 2.

Example XV

Example I was repeated, without toluene being added as solvent, with an L/Co ratio of 1.2 and a PE/Co ratio of 206 at a reaction pressure of 12.0 MPa and a temperature of 125° C. for 2 hours and 30 minutes. The reaction mixture contained 13.64 g of 3-pentenoic acid methyl ester, 0.96 g of nonane, 6.0 g of water, 0.29 mmol $Co_2(CO)_8$ and 0.66 mmol TPPTS. The results are presented in Table 2.

Example XVI

Example XV was repeated, the liner this time being filled with the water mixture separated in Example XV. The reaction mixture contained the aqueous phase of Example XV and 13.76 g of 3-pentenoic acid methyl ester, and 1.0 g of nonane. The results are presented in Table 2.

Example XVII

Example XVI was repeated, the liner this time being filled with the water mixture separated in Example XVI. The reaction mixture contained the aqueous phase of Example XVI and 13.60 g of 3-pentenoic acid methyl ester, and 0.99 g of nonane. The results are presented in Table 2.

TABLE 2

| Example | conv.[1] | tot-A | n-A | MV | Co |
|---|---|---|---|---|---|
| XII | 55 | 95 | 60 | 3 | <0.4 |
| XIII | 56 | 93 | 62 | 3 | <0.7 |
| XIV | 50 | 96 | 64 | 3 | <0.6 |
| XV | 28 | 95 | 63 | 3 | <0.7 |
| XVI | 27 | 95 | 63 | 4 | <0.5 |
| XVII | 30 | 96 | 64 | 3 | <0.6 |

[1] conv. + mol % conversion of 3-pentenoic acid methyl ester,
tot-A = mol % aldehydes relative to total of products,
n-A = % normal aldehydes of total of aldehydes,
MV = mol % methyl valerate relative to total of products,
Co = fraction (expressed in percents) of cobalt in organic phase after phase separation.

Examples XII–XVII show that the hydroformylation can successfully be effected in the absence of a solvent such as toluene.

Examples XV–XVII show that in the process according to the invention cobalt can be reused without any decrease in the selectivity and activity of the catalyst.

We claim:
1. A method for the preparation of an aldehyde in a process in which cobalt is being recycled which consists essentially of:
   (a) hydroformylating an ethylenically unsaturated compound in a reaction zone with carbon monoxide and hydrogen at a pressure higher than 5 MPa and at a temperature higher than 80° C. in the presence of an organic phase containing a cobalt carbonyl compound,
   (b) removing cobalt from said organic phase by contacting said organic phase with an aqueous mixture which is substantially immiscible with said organic phase under such conditions that practically all of the cobalt is incorporated in the aqueous mixture, wherein the pressure is reduced to a pressure below 5 MPa and simultaneously or afterwards the temperature is reduced to below 80° C., and wherein the aqueous mixture contains an organic ligand that is soluble therein and wherein the ligand is capable of forming a complex with cobalt whereby cobalt is removed from said organic phase to obtain a cobalt-containing aqueous mixture, wherein an amount of said aqueous mixture is used as to provide a weight ratio of said aqueous mixture to said organic phase of 1:10 to 10:1, and wherein the said organic ligand is represented by

or

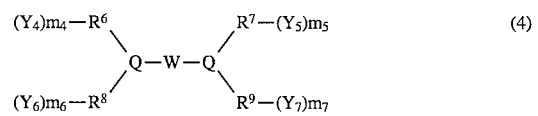

wherein
$R^3$, $R^4$ and $R^5$ of formula (3) and $R^6$, $R^7$, $R^8$ and $R^9$ of formula (4) independently represent a hydrocarbon group having 1–30 carbon atoms which is selected from the group consisting of alkyl, aryl, alkaryl, aralkyl, and cycloalkyl;

W in formula (4) represents bivalent organic bridging group;

Q represents an atom having coordination number 3 which is selected from the group consisting of P, As and Sb, $Y_1$, $Y_2$ and $Y_3$ of formula (3) and $Y_4$, $Y_5$ and $Y_6$ and $Y_7$ of formula (4) represent ionic groups that are substituted on the hydrocarbon group, which ionic groups are selected from the group consisting of —$SO_3M$, —$PO_3M$, $CO_2M$ and —$N(R^{10})_3X$, wherein M represents an inorganic or organic anion, M and X are selected so that the ligand is soluble in the aqueous mixture and $R^{10}$ represents a hydrocarbon group having 1 to 30 carbon atoms which is selected from the group consisting of alkyl, aryl, alkaryl, aralkyl and cycloalkyl, and $m_1$, $m_2$, $m_3$, $m_4$, $m_5$, $m_6$ and $m_7$ represent integers which independently are between 0 and 5, wherein at least one of $m_1$, $m_2$, and $m_3$ is not zero in formula (3), or at least one of $m_4$, $m_5$, $m_6$ and $m_7$ in formula (4) is not zero, the integer represented by $m_7$ through $m_7$ represent the number of ligand groups capable of ionization, and the number of ionizable ligand groups is sufficient to render the ligand soluble in the aqueous mixture;

(c) separating the cobalt-containing aqueous mixture from said organic phase;

(d) recovering the aldehyde from said organic phase;

(e) contacting the cobalt-containing aqueous mixture with the organic phase from (d), which organic phase is immiscible with the cobalt-containing aqueous mixture, under such conditions that at least a part of the cobalt from the aqueous mixture passes to the organic phase in the form of cobalt carbonyl to obtain a cobalt-containing organic mixture, wherein step (e) is conducted in the presence of carbon monoxide under a pressure greater than 2 MPa, and (f) recycling the organic mixture from step (e) to step (a).

2. The method according to claim 1, wherein the aqueous mixture in step (b) consists essentially of water.

3. The method according to claim 1 or 2, wherein the ethylenically unsaturated compound is an alkene or a cycloalkene having 3 to 30 carbon atoms.

4. The method according to claim 1 or 2, wherein the ethylenically unsaturated compound is a compound represented by the following chemical formula

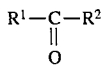

$$R^1-C-R^2$$
$$\parallel$$
$$O$$

wherein $R^1$ is a mono- or polyunsaturated, branched or unbranched, acyclic hydrocarbon group having 2 to 11 carbon atoms and $R^2$ represents an alkyl group having 1 to 8 carbon atoms or an aryl group having 6 to 10 carbon atoms.

5. The method according to claim 1 or 2, wherein the ethylenically unsaturated compound is a 2-pentenoic acid ester, a 3-pentenoic acid ester, or a 4-pentenoic acid ester or a mixture of any thereof.

6. The method according to claim 1 or 2, wherein the weight ratio of 1:5 to 5:1 of said aqueous mixture onto said organic mixture is used.

7. The method according to claim 1, wherein said organic ligand $R^6$, $R^7$, $R^8$ and $R^9$ of formula (4) represent phenyl groups.

8. The method according to claim 1 or 2, wherein said organic ligand W represents an alkylene group having 2 to 8 carbon atoms.

9. The method according to claim 1, wherein the organic ligand is a salt of a sulphonated or a carboxylated triaryl phosphine.

10. The method according to claim 1, wherein Q is a phosphorus atom.

11. The method according to claim 1, wherein the pressure in step (b) is reduced to a pressure between 0.01 and 5.0 MPa.

12. The method according to claim 1, wherein the pressure in step (b) is reduced to a pressure between 0.05 and 0.5 MPa.

13. The method according to claim 1 or 2, wherein the pressure in step (e) is between 5 and 30 MPa.

14. The method according to claim 1 or 2, wherein the temperature in step (e) is equal to or lower than the temperature in step (a).

15. The method according to claim 1, wherein step (a) is carried out in the presence of an organic solvent which is substantially immiscible with the aqueous mixture.

16. The method according to claim 15, wherein the organic solvent is an aromatic or paraffinic solvent.

17. The method according to claim 1, wherein the aldehyde in step (d) is recovered by means of distillation.

18. The method according to claim 1, wherein a part of the organic phase of step (a) is the organic phase of step (d) from which the aldehyde has been removed.

19. The method according to claim 1 or 2, wherein the ethylenically unsaturated compound is at least one selected from the group consisting of propene, butene, butadiene, pentene, hexene, octene, dodecene, cyclopentene, cyclohexene, cyclooctene, and cyclododecene.

20. The method according to claim 1, wherein the ethylenically unsaturated compound comprises a dialkene having 3 to 30 carbon atoms.

21. A method for the preparation of an aldehyde in a process in which cobalt is being recycled which consists essentially of:

(a) hydroformylating an ethylenically unsaturated compound in a reaction zone with carbon monoxide and hydrogen at a pressure higher than 5 MPa and at a temperature higher than 80° C. in the presence of an organic phase containing a cobalt carbonyl compound;

(b) removing cobalt from said organic phase by contacting said organic phase with an aqueous mixture which is substantially immiscible with said organic phase under such conditions that practically all of the cobalt is incorporated in the aqueous mixture, wherein the pressure is reduced to a pressure below 5 MPa and simultaneously or afterwards the temperature is reduced to below 80° C., and wherein the aqueous mixture contains an organic ligand that is soluble therein and wherein the ligand is capable of forming a complex with cobalt whereby cobalt is removed from said aqueous phase to obtain a cobalt-containing aqueous mixture, and wherein an amount of said aqueous mixture is used so as to provide a weight ratio of said aqueous mixture to said organic phase of 1:10 to 10:1, and wherein the said organic ligand is represented by

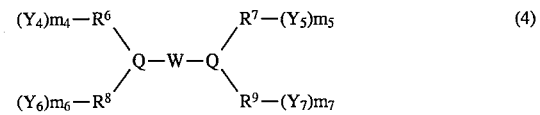

wherein $R^3$, $R^4$ and $R^5$ of formula (3) and $R^6$, $R^7$, $R^8$ and $R^9$ of formula (4) independently represent a hydrocarbon group having 1–30 carbon atoms which is selected from the group consisting of alkyl, aryl, alkaryl, aralkyl and cycloalkyl;

W in formula (4) represents a bivalent organic bridging group;

Q represents an atom having coordination number 3 which is selected from the group consisting of P, As and Sb, $Y_1$, $Y_2$ and $Y_3$ of formula (3) and $Y_4$, $Y_5$ and $Y_6$ and $Y_7$ of formula (4) represent ionic groups that are substituted on the hydrocarbon group, which ionic groups can are selected from the group consisting of —$SO_3M$, —$PO_3M$, $CO_2M$ and —$N(R^{10})_3X$, wherein M represents an inorganic or organic anion, M and X are selected so that the ligand is soluble in the aqueous mixture and $R^{10}$ represents a hydrocarbon group having 1 to 30 carbon atoms which is selected from the group consisting of alkyl, aryl, alkaryl, aralkyl and cycloalkyl, and $m_1$, $m_2$, $m_3$, $m_4$, $m_5$, $m_6$ and $m_7$ represent integers which independently are between 0 and 5, wherein at least one of $m_1$, $m_2$, and $m_3$ is not zero in formula (3), or at least one of $m_4$, $m_5$, $m_6$ and $m_7$ in formula (4) is not zero; the integers represented by $m_1$ through $m_7$ represent the number of ligand groups capable of ionization, and the number of ionizable ligand groups is sufficient to render the ligand soluble in the aqueous mixture;

(c) separating the cobalt-containing aqueous mixture from said organic phase, (d) recovering the aldehyde from said organic phase;

(e) contacting the cobalt-containing aqueous mixture with the organic phase from (d), which organic phase is immiscible with the cobalt-containing aqueous mixture, under such conditions that at least a part of the cobalt from the aqueous mixture passes to the organic phase in the form of cobalt carbonyl to obtain a cobalt-containing organic mixture, wherein step (e) the aqueous mixture is first treated with carbon monoxide and hydrogen at a pressure of 2 to 20 MPa and a temperature of 80° to 150° C., and subsequently the aqueous mixture is contacted with the organic phase in the absence of gaseous carbon monoxide and hydrogen; and (f) recycling the organic mixture from step (e) to step (a).

22. A method for the preparation of an aldehyde in a process in which cobalt is being recycled which consists essentially of:

(a) hydroformylating an ethylenically unsaturated compound in a reaction zone with carbon monoxide and hydrogen at a pressure higher than 5 MPa and at a temperature higher than 80° C. in the presence of an organic phase containing a cobalt carbonyl compound, to produce an aldehyde, wherein said unsaturated ethylenically unsaturated compound is represented by the formula:

$$R^1-\underset{\underset{O}{\|}}{C}-R^2$$

wherein $R^1$ is a mono- or polyunsaturated, branched or unbranched acyclic hydrocarbon group having 2 to 4 carbon atoms and $R^2$ represents an alkyl group having 1 to 8 carbon atoms or an aryl group having 6 to 10 carbon atoms;

(b) removing cobalt from said organic phase by contacting said organic phase with an aqueous mixture which is substantially immiscible with said organic phase under such conditions that practically all of the cobalt is incorporated in the aqueous mixture, wherein the pressure is reduced to a pressure below 5 MPa and simultaneously or afterwards the temperature is reduced to below 80° C., and wherein the aqueous mixture contains an organic ligand which is soluble in the aqueous mixture and wherein the ligand is capable of complexing with cobalt whereby cobalt is removed from said organic phase to obtain a cobalt-containing aqueous mixture, wherein an amount of said polar mixture is used so as to provide a weight ratio of said polar mixture to said organic phase of 1:10 to 10:1, and wherein the said organic ligand is represented by

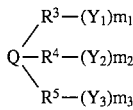

(3)

or

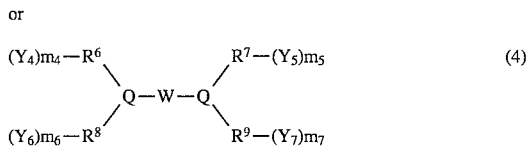

(4)

wherein $R^3$, $R^4$ and $R^5$ of formula (3) and $R^6$, $R^7$, $R^8$ and $R^9$ of formula (4) independently represent a hydrocarbon group having 1–30 carbon atoms which is selected from the group consisting of alkyl, aryl, alkaryl, aralkyl, and cycloalkyl;

W in formula (4) represents an alkylene group having 2 to 8 carbon atoms;

Q represents a P atom having coordination number 3, $Y_1$, $Y_2$ and $Y_3$ of formula (3) and $Y_4$, $Y_5$ and $Y_6$ and $Y_7$ of formula (4) represent ionic groups that are substituted on the hydrocarbon group, which ionic groups can are selected from the group consisting of $-SO_3M$, $-PO_3M$, $CO_2M$ and $-N(R^{10})_3X$, wherein M is the cation of an alkali metal or alkaline earth metal, X is an anion selected from the group consisting of sulphate, carbonate, chloride, acetate, and oxalate and $R^{10}$ represents a hydrocarbon group having 1 to 30 carbon atoms which is selected from the group consisting of alkyl, aryl, alkaryl, aralkyl, and cycloalkyl, and $m_1$, $m_2$, $m_3$, $m_4$, $m_5$, $m_6$ and $m_7$ represent integers which independently are between 0 and 5, wherein at least one of $m_1$, $m_2$, and $m_3$ is not zero in formula (3), or at least one of $m_4$, $m_5$, $m_6$ and $m_7$ in formula (4) is not zero, the integers represented by $m_1$ through $m_7$ represent the number of ligand groups capable of ionization, and the number of ionizable ligand groups is sufficient to render the ligand soluble in the aqueous mixture;

(c) separating the cobalt-containing polar mixture from said organic phase, (d) recovering the aldehyde from the at least essentially cobalt-free organic phase obtained in step (c);

(e) contacting the cobalt-containing aqueous mixture from step (b) with the organic phase from step (d), which organic phase is immiscible with the cobalt-containing aqueous mixture, under such conditions that at least a part of the cobalt from the aqueous mixture passes to the organic phase in the form of cobalt carbonyl to obtain a cobalt-containing organic mixture, and a residual aqueous mixture, wherein step (e) is conducted in the presence of carbon monoxide under a pressure greater than 2 MPa; and (f) recycling the organic mixture from step (e) to step (a).

23. The method according to claim 22, wherein after step (e), the residual aqueous mixture is recycled to step (b).

24. A method for the preparation of an aldehyde in a process in which cobalt is being recycled which consists essentially of:

(a) hydroformylating an ethylenically unsaturated compound in a reaction zone with carbon monoxide and hydrogen at a pressure higher than 5 MPa to 30 MPa and at a temperature of between 60° C. to 200° C. in the presence of an organic phase containing a cobalt carbonyl compound, the amount of said ethylenically unsaturated compound relative to carbon monoxide is in a molar ratio of 1:10 to 10:1;

(b) removing cobalt from said organic phase by contacting said organic phase with an aqueous mixture which is substantially immiscible with said organic phase under such conditions that practically all of the cobalt is incorporated in the aqueous mixture, wherein the pressure is reduced to a pressure below 5 MPa and simultaneously or afterwards the temperature is reduced to 20° C. to below 80° C., and wherein the aqueous mixture contains an organic ligand that is soluble therein and wherein the ligand is capable of forming a complex with cobalt whereby cobalt is removed from said organic phase to obtain a cobalt-containing aqueous mixture, wherein an amount of said aqueous mixture is used as to provide a weight ratio of said aqueous mixture to said organic phase of 1:10 to 10:1, and wherein the said organic ligand is represented by

(3)

or

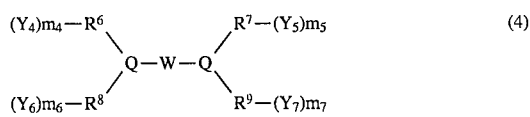

(4)

wherein $R^3$, $R^4$ and $R^5$ of formula (3) and $R^6$, $R^7$, $R^8$ and $R^9$ of formula (4) independently represent a hydrocarbon group having 1–18 carbon atoms which is selected from the group consisting of ethyl, methyl, propyl, butyl, hexyl, cyclohexyl and phenyl, wherein at least two of $R^3$, $R^4$ and $R^5$ represent phenyl or at least three of $R^6$, $R^7$, $R^8$ and $R^9$ represent phenyl;

W in formula (4) represents bivalent organic bridging having 1–30 carbon atoms group;

Q represents an atom having coordination number 3 which is selected from the group consisting of P, As and Sb;

$Y_1$, $Y_2$ and $Y_3$ of formula (3) and $Y_4$, $Y_5$ and $Y_6$ and $Y_7$ of formula (4) represent ionic groups that are substituted on the hydrocarbon group, which ionic groups are selected from the group consisting of $-SO_3M$, $-PO_3M$, $CO_2M$ and $-N(R^{10})_3X$, wherein M represents an inorganic or organic anion, M and X are selected so that the ligand is soluble in the aqueous mixture and $R^{10}$ represents a hydrocarbon group having 1 to 30 carbon atoms which is selected from the group consisting of alkyl, aryl, alkaryl, aralkyl and cycloalkyl; and $m_1$, $m_2$, $m_3$, $m_4$, $m_5$, $m_6$ and $m_7$ represent integers which independently are between 0 and 5, wherein at least one of $m_1$, $m_2$, and $m_3$ is not zero in formula (3), or at least one of $M_4$, $m_5$, $m_6$ and $m_7$ in formula (4) is not zero, the integer represented by $m_1$ through $m_7$ represent the number of ligand groups capable of ionization, and the number of ionizable ligand groups is sufficient to render the ligand soluble in the aqueous mixture;

(c) separating the cobalt-containing aqueous mixture from said organic phase;

(d) recovering the aldehyde from said organic phase;

(e) contacting the cobalt-containing aqueous mixture with the organic phase from (d), which organic phase is immiscible with the cobalt-containing aqueous mixture, under such conditions that at least a part of the cobalt from the aqueous mixture passes to the organic phase in the form of cobalt carbonyl to obtain a cobalt-containing organic mixture, wherein step (e) is conducted in the presence of carbon monoxide under a pressure greater than 2 MPa, and (f) recycling the organic mixture from step (e) to step (a).

25. A method according to claim 1, wherein the temperature in step (e) is equal to or lower than the temperature in step (a).

* * * * *